United States Patent [19]
Hayasuke et al.

[11] Patent Number: 5,503,993
[45] Date of Patent: Apr. 2, 1996

[54] METHOD OF PREPARING FOREIGN PROTEIN IN YEAST, RECOMBINANT DNA, TRANSFORMANT

[75] Inventors: Naofumi Hayasuke; Yukimitsu Nakagawa; Yutaka Ishida; Ken Okabayashi; Kohji Murakami, all of Osaka; Kiyoshi Tsutsui, Kyoto; Kazuo Ikegaya, Tokyo; Hitoshi Minamino, Osaka; Sadao Ueda, Kyoto; Haruhide Kawabe, Osaka; Hirofumi Arimura, Osaka; Atusi Masaki, Osaka, all of Japan

[73] Assignee: The Green Cross Corporation, Osaka, Japan

[21] Appl. No.: 445,783

[22] Filed: May 22, 1995

Related U.S. Application Data

[63] Continuation of Ser. No. 913,785, Jun. 30, 1992, abandoned, which is a continuation of Ser. No. 190,553, May 5, 1988, abandoned.

[30] Foreign Application Priority Data

Dec. 2, 1987 [JP] Japan ................................. 62-306674
Feb. 26, 1988 [JP] Japan ................................. 63-45605

[51] Int. Cl.$^6$ ..................... C12N 15/14; C12N 15/81; C07K 14/765
[52] U.S. Cl. ..................... 435/69.8; 435/69.6; 435/69.7; 435/172.3; 435/254.2; 435/254.21; 435/320.1; 536/23.4; 536/23.5; 530/363
[58] Field of Search .................... 435/69.1, 69.6, 435/69.7, 69.8, 254.11, 254.2, 254.4, 172.3, 320.1; 536/23.4, 23.5; 530/363

[56] References Cited

U.S. PATENT DOCUMENTS 4,775,622 10/1988 Hitzeman et al. ..................... 435/69.1

FOREIGN PATENT DOCUMENTS 0038182 10/1981 European Pat. Off. .
0079739 5/1983 European Pat. Off. .
0206733 12/1986 European Pat. Off. .
0236210 9/1987 European Pat. Off. .

OTHER PUBLICATIONS

Bathurst et al., Science, vol. 235 pp. 348–350 1987.
Etchewery et al Biotechnology vol. 4 pp 726–730 1986.
Meade et al. 1985 Citus Corp. Provided as Biotech Abstr. Acc #86–04642.
Kaiser et al. Science 235:312 (1987). Provided as BIOSIS Abstr. Acc #8307–5440.
Biotechnology Abstract Acc #: 89–06780, Hinnen (1987) Eur. Congr. Biotechnol. vol. 2,4.
Biotechnology Abstract Acc #: 88–00676, King et al. (1987) (Int. Congr. Microbiol. 14 Meet., 259).
Proc. Natl. Acad. Sci. U.S.A., vol. 79, Jan 1982 pp. 71–75.
Eur. J. Biochem, vol. 98, No. 2, 1979, pp. 477–485.
Okabayashi et al., Secretory Expression of the Human Serum Albumin Gene in the Yeast, *Saccharomyces cerevisiae*, J. Biochem. 110, 103–110 (1991).

*Primary Examiner*—Jacqueline M. Stone
*Assistant Examiner*—John LeGuyader
*Attorney, Agent, or Firm*—Sughrue, Mion, Zinn, Macpeak & Seas

[57] ABSTRACT

A method for preparing foreign protein in yeast using an expression recombinant DNA comprising DNA encoding the serum albumin signal peptide adjacent to DNA encoding the foreign protein is disclosed.

4 Claims, 9 Drawing Sheets

METHOD OF PREPARING FOREIGN PROTEIN IN YEAST, RECOMBINANT DNA, TRANSFORMANT

This is a continuation of application Ser. No. 07/913,785 filed Jun. 30, 1992, now abandoned, which is a continuation of 07/190,553 filed on 5 May 1988 now abandoned.

FIELD OF THE INVENTION

This invention relates to a method for preparing foreign protein in yeast using an expression recombinant DNA comprising DNA encoding the serum albumin signal peptide adjacent to DNA encoding the foreign protein.

BACKGROUND OF THE INVENTION

In the production of specific proteins in a recombinant host by recombinant DNA technology, there are many advantages to having the host express and secrete the desired protein. That is, when a desired protein is expressed directly within the host cell, if there is any toxicity which inhibits growth or compromises the survival of the host cell, this toxicity can be avoided by the secretion of the protein. Even when there is no toxicity, as the protein accumulates in the host cell, it may inhibit the host cell growth. This, too, can be avoided by secretory expression. In addition, systems which accumulate protein in the host cell may also denature it, rendering it insoluble. This problem also can be avoided by secretory expression. Moreover, when commercially producing protein by recombinant DNA technology in a system which accumulates the desired protein intracellularly, it is necessary to destroy the cell in order to refine the protein, and it must be purified from the debris of the cellular destruction. This makes it difficult to obtain a protein of high purity. On the other hand, when producing a protein by a secretory expression system the protein only must be harvested from the culture broth, minimizing the problem of separating impurities derived from the recombinant host. This is a great advantage. Finally, most protein undergoes some modification, such as the addition of a sugar moiety, the formation of a disulfide bond, activation by limited hydrolysis of the inert proprotein, phosphorylation of specific amino acids, or carboxylation before activation. Some of these functions are performed by the themselves, and several of these modifications take place in the process of secretion. Therefore, a system which produces protein by secretory expression, as compared to a system which accumulates protein intracellularly, may be expected to generate proteins having a structure and function much close to the native protein.

Some things are known about the properties of the signal peptide, and the characteristics of its amino acid sequence seem to be as follows. There are many basic amino acids near the N-terminal, and there are many polar amino acids near the portion which is digested by signal peptidase on the C-terminal side, while a sequence hydrophobic amino acids fill in the space between these two areas. The basic amino acids near the N-terminal interact with the phospholipids on the internal surface of the cell membrane, and the sequence of hydrophobic amino acids in the middle region playes an important role in passing the protein through the cell membrane. The polar amino acids at the C-terminal are believed to play some role in recognition during digestion by signal peptidase. These characteristics are extremely similar from procaryotes to higher animals, suggesting a common mechanism for protein secretion. (M. S. Briggs and L. M. Gierasch, Adv. Protein Chem., 38, 109–180 (1986); G. yon Heijne, EMBO J., 3, 2315–2318 (1984)).

Human serum albumin is encoded on the gene as a prepro type protein (see Japanese Patent Application (OPI) No. 29985/87 (the term OPI used herein means an unexamined published application.) or EP-A-206733; A. Dugaiczyk et al. Proc. Natl. Acad. Sci. USA, 79, 71–75 (1982)). The DNA and amino acid sequence in the vicinity of the N-terminal of mature human serum albumin beginning from the signal peptide essential for secretion are shown in Table 1 below.

TABLE 1

| |————Signal peptide———————————————— | | | Propeptide | | |
| −18 | | −1 −6 | | −1 +1 |

Met Lys Trp Val Thr Phe Ile Ser Leu Leu Phe Leu Phe Ser Ser Ala Tyr Ser Arg Gly Val Phe Arg Arg Asp Ala His
ATGAAGTGGGTAACCTTTATTTCCCTTCTTTTTCTCTTTAGCTGCGCTTATTCCAGGGGTGTGTTTCGTCGAGATGCACAC

The signal peptide, composed of 18 amino acid is removed at the time of secretion. The propeptide, composed of 6 amino acids, is removed by processing, and mature human serum albumin, composed of 585 amino acids, and having an N-terminal amino acid sequence of Asp-Ala-His-Lys-Ser . . . , is obtained.

Since yeast secrete less extracellular proteases and are capable of adding sugar moieties to its secreta, yeast is excellent for the secretory expression of foreign proteins.

Several cases of signal peptides which contributes to the secretory expression in cells other than yeast, but which also function in yeast, have been reported. Examples include the secretory expression in yeast of human lysozyme using the chicken lysozyme signal peptide (Jigami, BIOINDUSTRY, 4, 117–123 (1987)), secretory expression in yeast of thaumatin using the signal peptide for plant protein thaumatin (L. Edens, I. Bom, A. M. Ledeboer, J. Maat, M. Y. Toonen, C. Visser and C. T. Verrips, Cell, 37, 629–633 (1984)), and secretory expression in yeast of human interferon using the signal peptide for human interferon-α (R. A. Hitzeman, D. W. Leung, L. J. Perry, W. J. Kohr, H. L. Levine and D. V. Doeddel, Science, 219, 620–625 (1983)).

The truth is, however, that the signal peptide contributing to secretory expression in cells other than yeast does not always function in yeast.

SUMMARY OF THE INVENTION

Therefore, a primary object of this invention is to provide a method for expressing and secreting foreign protein efficiently in yeast, the signal peptide gene functionable in yeast for secretory expression, the vector to be used in this method, and the transformant transformed by this vector.

The above-described object of the present invention has been met in one embodiment by a method for preparing foreign protein comprising expressing and secreting said foreign protein by yeast transformed by a recombinant DNA comprising the serum albumin signal peptide gone adjacent to the gene of said foreign protein. In a second embodiment, the present invention relates to a serum albumin signal peptide gene and derivatives thereof. In a third embodiment, the present invention relates to a recombinant DNA for transforming yeast comprising DNA encoding the serum albumin signal peptide adjacent to DNA encoding a foreign protein. In a fourth embodiment, the present invention relates to a strain of yeast transformed by a recombinant DNA comprising DNA coding for the serum albumin signal peptide adjacent to DNA encoding a foreign protein.

Practically, human-derived, rat-derived and bovine-derived preparations can be used.

Examples of the amino acid sequences of such signal peptides are known to include;

| Met | Lys | Trp | Val | Thr | Phe | Ile | Ser | Leu | Leu | Phe | Leu |
| Phe | Ser | Ser | Ala | Tyr | Ser | derived from humans; |
| Met | Lys | Trp | Val | Thr | Phe | Leu | Leu | Leu | Leu | Phe | Ile |
| Ser | Gly | Ser | Ala | Phe | Ser | derived from rats; and |
| Met | Lys | Trp | Val | Thr | Phe | Ile | Ser | Leu | Leu | Leu | Leu |
| Phe | Ser | Ser | Ala | Tyr | Ser | derived from cows. |

However, preferably, the human serum albumin signal peptide gene is used and the 2nd amino acid and the last five amino acids can be changed by Y and Xs as the following sequence.

| Met | Y | Trp | Val | Thr | Phe | Ile | Ser | Leu | Leu | Phe | Leu |
| Phe | $X_5$ | $X_4$ | $X_3$ | $X_2$ | $X_1$ | | | | | | |

DETAILED DESCRIPTION OF THE INVENTION

The recombinant DNA of this invention comprises the serum albumin signal peptide gene, the foreign protein gene, a promoter, a terminator, and the plasmid DNA or chromosome DNA.

The origin of the serum albumin signal peptide gene is not specifically defined as long as it is derived from mammals.

wherein Y represents Lys, Arg or His and preferably represents Lys; $X_5$ represents Ala, Pro or Ser; $X_4$ represents Lys, Gly or Ser; $X_3$ represents Ala, Val or Cys and preferably represents Val or Cys; $X_2$ represents Tyr, Trp or Ser; and $X_1$ represents Ser, Ala or Gly and preferably represents Ala or Gly. Preferable examples of amino acid sequences of the signal peptides are shown in Table 2 below.

TABLE 2

| Sequence No. | Y | $X_5$ | $X_4$ | $X_3$ | $X_2$ | $X_1$ |
| --- | --- | --- | --- | --- | --- | --- |
| Sequence 1 | Lys | Ser | Ser | Val | Tyr | Ala |
| Sequence 2 | Lys | Ala | Lys | Val | Ser | Ala |
| Sequence 3 | Lys | Pro | Gly | Cys | Trp | Ala |
| Sequence 4 | Lys | Pro | Gly | Val | Trp | Ala |

The serum albumin signal peptide gene may possess a DNA sequence which can be expressed by the amino acid sequence shown above, and one example is having the following DNA sequence.

ATGAAGTGGGTAACCTTTATTTCCCTT
CTTTTCTCTTTAGCTCGGCTTATTCC

Preferable codons corresponding to each amino acid are set forth below.

| | | |
| --- | --- | --- |
| Ala: GCT or GCC, | Cys: TGT, | Asp: GAC, |
| Glu: GAA, | Phe: TTC, | Gly: GGT, |
| His: GAC, | Ile: ATT or ATC, | Lys: AAG, |
| Leu: TTG, | Met: ATG, | Asn: AAC, |
| Pro: CCA, | Gln: CAA, | Arg: AGA, |
| Ser: TCT or TCC, | Thr: ACT or ACC, | Val: GTT or GTC, |
| Trp: TGG, | Tyr: TAC | |

As the foreign protein in this invention, human serum albumin, interferon-α, -β, or -γ, urokinase, growth hormone, insulin, Factor VIII, EPO, h-ANP, M-CSF and various lymphokines may be used.

In the case of human serum albumin, pre type, pro type, or prepro type may be used, and in the case of urokinase, pro type or any other type may be used. Among foreign proteins, in particular, a mature human serum albumin gene is preferable. According to the present invention, in the case that the mature human serum albumin gene is positioned immediately downstream to the serum albumin signal peptide gene, a substantial quantity of albumin can be produced.

Such foreign protein genes have been described in Japanese Patent Application (OPI) No. 29985/87 or EP-A-206733 (human serum albumin), Japanese Patent Application (OPI) No. 185189/86 or DE-A-3603958 (interferon-α), Japanese Patent Application (OPI) No. 108397/86 or EP-A-190686 (interferon-γ), Japanese Patent Application (OPI) No. 180591/85 or EP-A-154272 (urokinase), EP-A-160457 (Factor VIII), EP-A-148605 (EPO), WO85-4670 (h-ANP), WO86-4607 (M-CSF), and others.

In the above publications, the inventions are described as plasmids containing foreign protein genes.

The recombinant DNA for transforming yeast in this invention is prepared by linking the foreign protein gene downstream to the serum albumin signal peptide gene.

The promoter and terminator are not specifically limited to those found in yeast.

Acceptable promoters include PGK promoter (Nucleic Acid Res., 10(23), 7791 (1982)), ADH promoter (ibid.), phoE (5) promoter (J. MOl. Biol., 163(4), 513 (1983)), GAL1 promoter (Mol. Cell. Biol., 4(11), 2467 (1984)), GAL10 promoter (EP-A-132309) and GAP-DH promoter (J. Biol. Chem., 258, 5291 (1983)). Among these promoters, GAL1 promoter is particularly preferable.

The promoter is positioned upstream to the serum albumin signal peptide gene.

Acceptable terminators include the phoE(5) terminator (Cell, 12, 721–732 (1977)) and the GAP-DH terminator (J. Biol. Chem., 254, 9839–9845 (1979)).

The terminator is positioned downstream to the foreign protein gene.

The promoter and terminator may be obtained in a form already incorporated into plasmids.

The plasmid DNA must be capable of self-replication in yeast.

Acceptable examples are pJDB207 (Amersham) and pJDB219 (Amersham).

The recombinant plasmid of this invention is obtained either by cleaving a DNA sequence composed of the serum albumin signal peptide gene-foreign protein gene, a DNA sequence containing the promoter, and a DNA sequence containing the terminator from the above plasmid groups by a restriction enzyme and coupling (connecting) them to incorporate them into a proper plasmid, or by cleaving one DNA sequence and then incorporating it into another plasmid.

Also, the recombinant chromosome of this invention is obtained by insertion of a DNA sequence comprising the serum albumin signal peptide gene-foreign protein gene, a DNA sequence containing the promoter, and a DNA sequence containing the terminator into the yeast chromosome. The detail methods have been described in Proc. Natl. Acad. Sci. USA, 78, 6354–6358 (1981) and Method Enzymol., 101, 228–245 (1983).

The DNA sequence on the plasmid or the chromosome is arranged, from upstream to downstream, in the order of the promoter, serum albumin signal peptide gene, foreign protein gene, and terminator.

As the marker for selecting the desired plasmid, it is also possible to incorporate an antibiotic (tetracycline, ampicillin, kanamycin) resistance gene, or a gene to compensate for a nutritional requirement of the host. The method of preparing a transformant by this recombinant plasmid or the method of preparing a foreign protein is as follows.

The recombinant plasmid is introduced into the host cell i.e., yeast. Practically, a strain having a variation which is complemented by the selective marker gene carried by the plasmid to be inserted, for example, *Saccharomyces cerevisiae* AH22 (a, his4, leu2, can1) which is a leucine-requiring variant is acceptable for use.

Transformation of the host cell (yeast) is conducted by an established method, for example, the calcium phosphate sedimentation method, protoplast-polyethylene glycol fusions method, electropolation method.

The transformant is incubated in an established culture medium for the growth of the host cell. Practical examples of culture medium are YNB liquid culture medium (0.7 w/v % yeast nitrogen base (Difco Co.) and 2 w/v % glucose), YPD liquid culture medium (1 w/v % yeast extract (Difco), 2 w/v % polypeptone (Daigo Eiyo Sha), 2 w/v % glucose) and others.

Incubation is performed for 20 to 100 hours, usually at 15° to 43° C. (preferably about 30° C.), while being aerated or stirred as required.

After cultivation, the culture supernatant is recovered, and the foreign protein is purified by an established method, such as affinity chromatography or fractionation.

By using the method of this invention, a desired foreign protein can be produced by secretory expression. Compared with the system intracellular accumulation, production of the protein possessing structure and function much close to the native protein may be expected.

Additionally, in the system of intracellular accmulation, it is necessary to destroy the cells to refine the protein and to purify the protein from the liquid which contains debris, but this type of purification process is unnecessary when the method of this invention is used.

The use of the serum albumin signal peptide in expression of the protein also allows the development of the new secretory expression method. This increases the potential usefulness of this invention considerably.

This invention is described in further detail below by referring to the following Example, which, however, is not intended to limit this invention in any respect.

Many of the techniques, reactions and analytical methods used in this invention are well known in the art. Unless otherwise specified, all enzymes can be obtained from commercial supply sources: for example, Takara Shuzo, Japan; New England Biolabs (NEB), Massachusetts, U.S.A; Amersham, England; and Bethesda Research Laboratories (BRL), Maryland, U.S.A.

Buffer solutions for enzymatic reactions and reaction conditions conformed to the recommended specifications of the manufacturers of the enzymes unless otherwise noted.

The transformation method of *Escherichia coli* by plasmid, colony hybridization, electrophoresis, and DNA recovery method from gels were conducted in accordance with the methods mentioned in "Molecular Cloning", Cold Spring Harbor Laboratory (1982). Yeast was transformed by the method stated in "Method in Yeast Genetics", Cold Spring Harbor Laboratory (1981).

EXAMPLE

Cloning of yeast GAL1, 10 promoters (A) Preparation of yeast chromosomat DNA library The chromosomal DNA of the yeast *Saccharomyces cerivisiae* GRF18 PH080 cir$^0$ strain (as described in EP-A-0180958 was extracted and purified by the method described by R. Cryer et al., (Method Enzymol., 12, 39 (1975)).

According to M. Mohnson and R. W. Davis (Mol. Cell. Biol., 4, 1440–1448 (1984)), the yeast GAL1, 10 promoter regions are located on the yeast chromosome, and when it is digested by the restriction enzymes EcoRI and XbaI, DNA segments of about 1 kb are obtained. Hence, yeast chromosomal DNA, extracted and purified as described above, was digested by EcoRI and XbaI, and DNA segments of about 1 kb were isolated by electrophoresis. These segments were mixed with plasmid pUC19 (BRL) which was digested by EgoRI and XbaI, and dephosphorylated at its 5' terminal with alkaline phosphatase derived from calf intestines (CIP). These were ligated using the ligation kit (Takara Shuzo). This product was introduced into *Escherichia coli* JM109 (Takara Shuzo). The transformant was applied to a YT agar plate containing 0.004 w/v % X-gal (5-bromo-4-chloro-3-indolyl-β-galactoside) and 1 mM IPTG (isopropyl-β,D-thiogalactopyranoside), and was incubated overnight at 37° C. (To prepare the agar plate 8 g of polypeptone, 5 g of yeast extract, and 5 g of sodium chloride were dissolved in water to make up 1 liter and 12 g of agar powder was added. After sterilization in an autoclave, the mixture was dispensed into plastic Petri dish and solidified; X-gal and IPTG were added after autoclaving once the culture medium had cooled.)

White and blue colonies appeared, and only the white clonies having the DNA inserts were used. (The desired transformant produced white colonies since the recombinant plasmid inserted therein had no lac Z gene.) One hundred colonies were inoculated onto an L-agar plate containing 40 μg/ml ampicillin by a sterilized toothpick. (To prepare the agar plate 0.62 g of tris base, 10 g of polypeptone, 5 g of yeast extract, and 5 g of sodium chloride were dissolved in water to make up 1 liter, and 12 g of agar powder was added. The mixture was sterilized in an autoclave, dispensed into plastic Petri dish and solidified: ampicillin added, after autoclaving once the medium had cooled.) This L-agar plate was incubated overnight at 37° C. By this method, a library consisting of about 5,000 colonies was prepared. The formed colonies were transferred to a nitrocellulose filter, dipped in a solution of 0.5M sodium hydroxide and 1.5M sodium chloride to denature the DNA, and were neutralized in a solution of 1.5M sodium chloride and 0.5M trishydrochloric acid at pH 7.5. The *E. coli* debris was washed with 2×SSC (0.3M sodium chloride, 0.03M sodium citrate at pH 7.0) and removed, and after drying the filter in air, it was subjected to vacuum drying for 2 hours at 80° C.

(B) Preparation of the probe

Part of base sequence of the gene coding for the GAL1, 10 promoters was synthesized by the phosphoramidite method using a DNA synthesizer, Applied Biosystem Co. model 381A. Its sequence is shown below.

5'-CTCTATACTTTAACGTCAAG-3'

The sequence was subjected to electrophoresis using 7M urea-20 w/v % polyacrylamide gel and purified. The 5' terminal of the purified DNA sequence was labeled radioactively by [γ-$^{32}$P] ATP and T4 polynucleotide kinase. The reaction using 10 pmoles of synthetic DNA, 250 μCi of [γ-$^{32}$P] ATP, and 8 units of T4 polynucleotide kinase, resulted in a synthetic DNA probe terminally labeled with $^{32}$P (2×10$^7$ cpm (Cerenkov count)). The synthetic DNA probe was purified by NENSORB 20 (Du Pont).

(C) Screening of AL1, 10 promoters

Nitrocellulose filters having the DNA fixed as described in step (A) were placed in vinyl bags with each set containing 10 filters, and the following process carried out. Ten milliliters of prehybridization solution composed of 6×SSC, 0.1 w/v % SDS, and 20 μg/ml of salmon sperm DNA cooled on ice after heating for 5 minutes at 100° C. was put in a vinyl bag which was sealed and incubated for 3 hours at 40° C. The prehybridization solution was then discarded and 10 ml of hybridization solution was added and incubated overnight at 40° C. The hybridization solution contained 6×SSC, 0.1 w/v % SDS, 100 μg/ml salmon sperm DNA, and 7.5×10$^5$ cpm/ml $^{32}$P-probe. After incubation, the filter was transferred to a beaker and washed in 6×SSC, 0.1 w/v % SDS for 30 minutes at 50° C., in 2×SSC and 0.1 w/v % SDS for 30 minutes at 50° C., in 2×SSC and 0.1 w/v % SDS for 30 minutes at 50° C., and finally in 0.1×SSC and 0.1 w/v % SDS for 30 minutes at 50° C. The washed filter was dried in air and subjected to autoradiography after applying spotting marks of 100– 200 cpm. As a result, two positive clones were obtained. One of the clones was subjected to shaking culture overnight at 37° C. in super broth containing 40 μg/ml of ampicillin. (To prepare the super broth 12 g of bactotrypton, 24 g of yeast extract, and 5 ml of glycerol were dissolved in water to make up 900 ml, which was sterilized by autoclave to obtain solution A. Then, 3.81 g of potassium dihydrogen phosphate and 12.5 g of potassium monohydrogen phosphate were dissolved in water to make up 100 ml, which was sterilized by autoclave to obtain solution B. These solutions A and B were mixed in a ratio of 9:1 by v/v.) Then, the plasmid DNA was extracted and purified by the alkaline-SDS method.

When part of the base sequence of this plasmid DNA (pGAL11, FIG. 1). was examined by the dideoxy method, the results coincided with the reported sequence by M. Johnston and R. W. Davis (Mol. Cell, Biol., 4, 1440–1448, (1984)). That is, it was found that pGAL11 possessed the GAL1 promoter in the direction of the XbaI site from the EcoRI site, and the GAL10 promoter in the opposite direction.

(D) Conversion of pGAL11 from the XbaI site to the BamHI site

When ligating the promoter sequence on pGAL11 with the DNA sequence coding for the signal peptide and human serum albumin, it is not convenient to have an intervening XbaI site because the XbaI site is present on the human serum albumin gene. Therefore, the XbaI site was converted to the BamHI site as follows.

Figure 1:
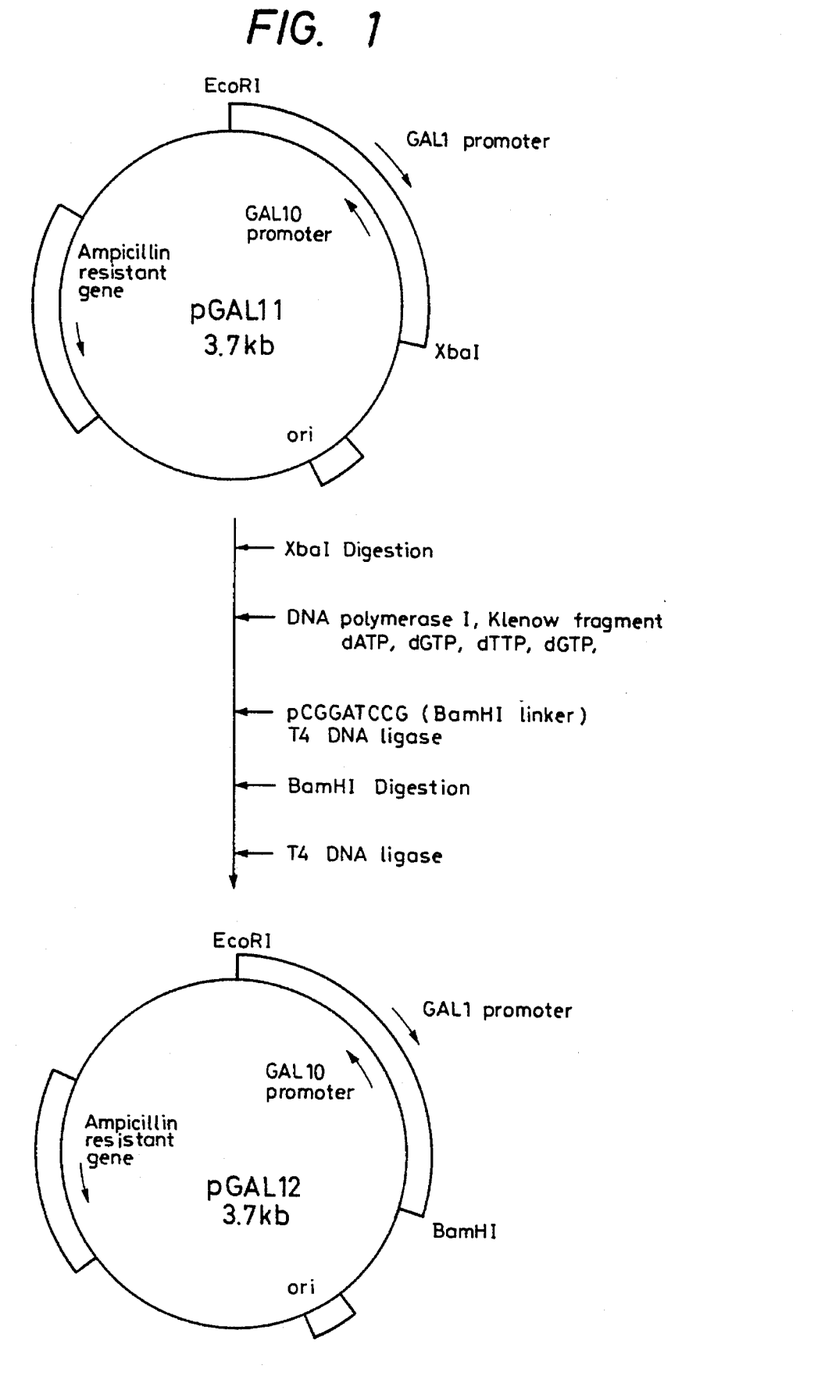
FIG. 1 shows the procedure for making pGAL12 from pGAL11 possessing the GAL1, 10 promoters.

After digesting pGAL11 by XbaI, the sticky end was repaired by *E. coli*-derived DNA polymerase I, Klenow fragment, in the presence of dGTP, dATP, dTTP, dCTP. To this DNA fragment, the BamHI linker pCGGATCCG having a phosphorylated 5' terminal was added and was ligated by T4 DNA ligase. After then digesting with BamHI, ligation was again carried out with T4 DNA ligase and the resulting plasmid introduced into *E. coli* HB101 (EP-A-13828). From the resulting transformants, a clone having plasmid pGAL12 (as shown in FIG. 1) was obtained. By digesting pGAL12 by EcoRI and BamHI, the GAL1 and GAL10 promoters could be isolated as a DNA fragment of about 1 kb.

Figure 2:
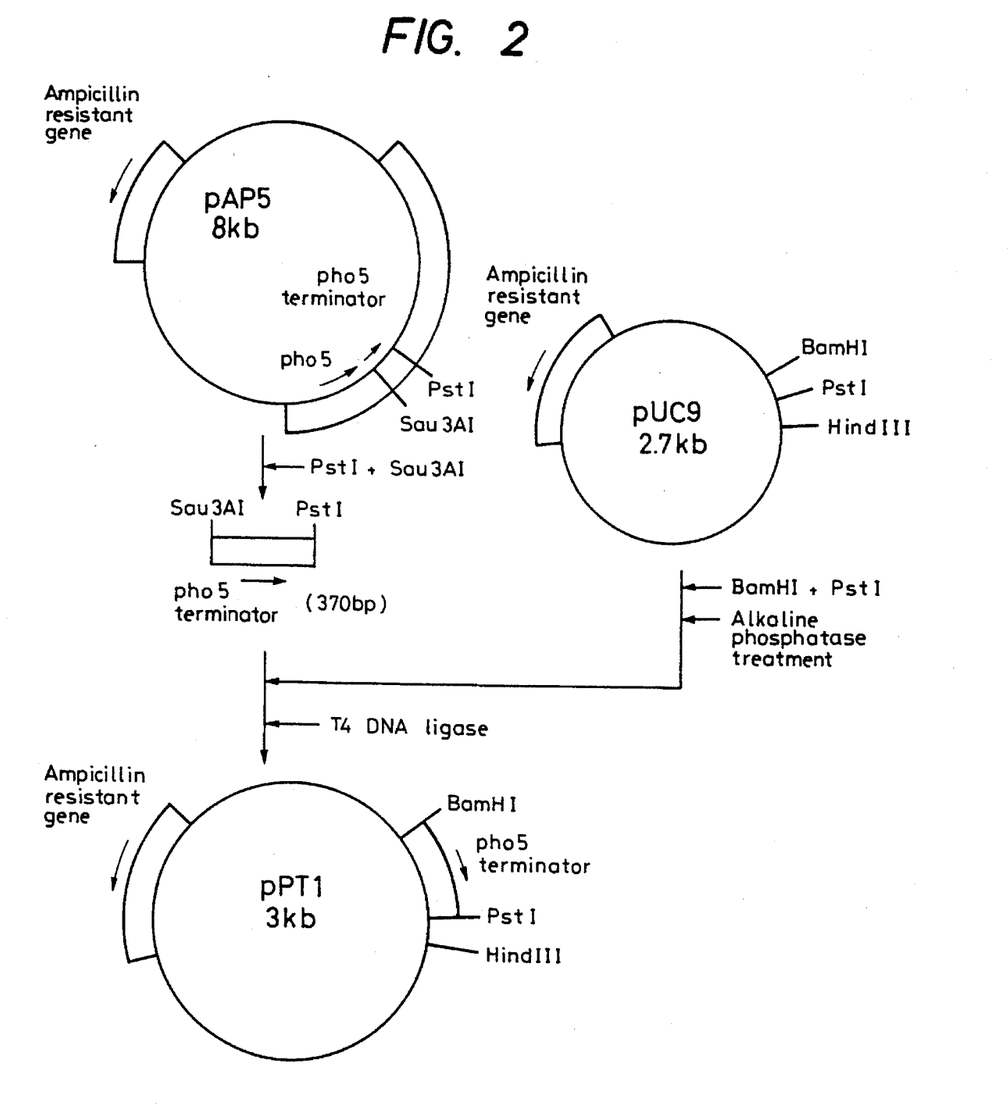
FIG. 2 shows the procedure for making pPT1, containing only the pho5 terminater, from pAP5 and pUC9 containing the entire pho5 gene.

(E) Preparation of *E. coli*-yeast shuttle vector pPT2 possessing a yeast pho5 terminator The plasmid pAP5 which has encoded the *Saccharomyces serevisiae* pho5 gene is disclosed in Japanese Patent Application (OPI) No. 151183/87 or EP-A-216573. This plasmid was digested by the restriction enzymes Sau3AI and PstI, and the DNA fragment which has encoded the pho5 terminator, about 370 bp, was isolated by electrophoresis (FIG. 2). The commercially available pUC9 (BRL) was then digested with BamHI and pstI, treated with alkaline phosphatase, and ligated with the 370 bp DNA fragment. The base sequence at the Sau3AI cleavage site of the 370 bp fragment was

GATCC . . .

G . . .

and when it was ligated with the sticky end of the BamHI, the BamHI site was regenerated. Therefore, by digesting plasmid pPT1 obtained in the above ligation reaction with BamHI and PstI, or by digestion with BamHI and HindIII, a DNA fragment possessing a 370 bp pho5 terminator was obtained (FIG. 2).

Figure 3:
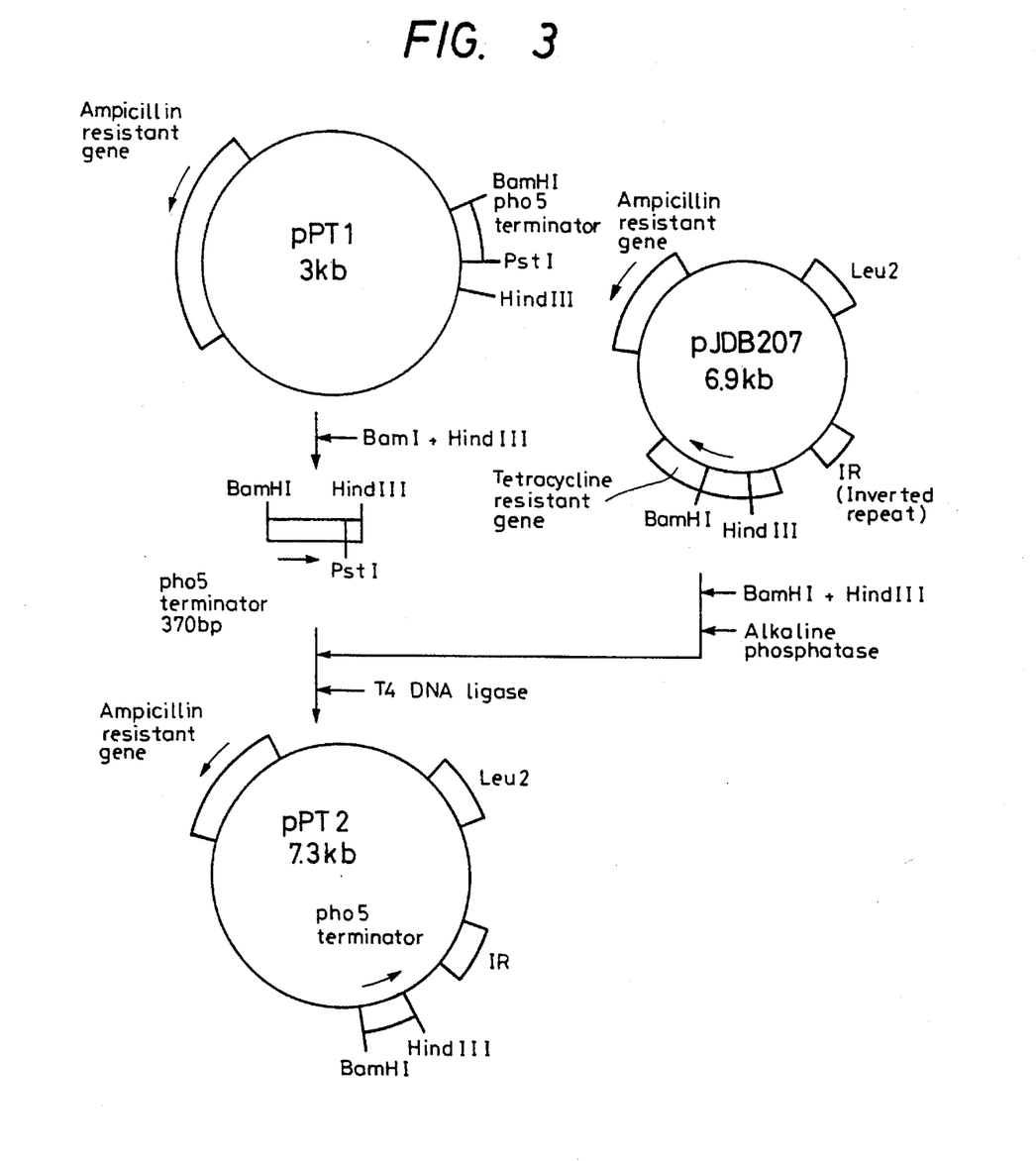
FIG. 3 shows the procedure for making pPT2 from pJDB207.

The commercially available shuttle vector pJDB207 (FIG. 3) is self-replicating in *E. coli* and yeast. After digestion with BamHI and HindIII, it was treated with alkaline phosphatase. After digesting pPT1 with BamHI and HindIII, the DNA fragment having the 370 bp pho5 terminator was isolated by electrophoresis and was ligated with pJDB207. From the resulting transformants, a clone having plasmid pPT2 (as shown in FIG. 3) was obtained. pPT2 is an *E. coli*-yeast shuttle vector possessing a pho5 terminator. In *E. Coli*, it possesses an ampicillin resistance marker with β-lactamase activity and in yeast it has a marker to compensate for a leucine nutritional requirement.

(F) Human serum albumin gene

Figure 4:
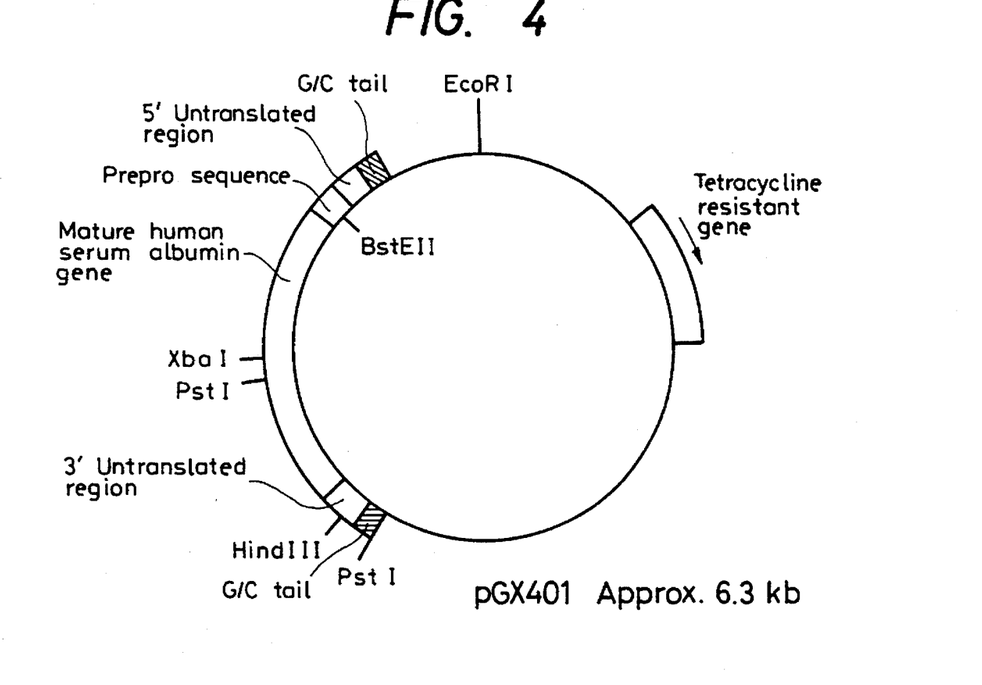
FIG. 4 and FIG. 5 show the restriction enzyme map of pGX401 containing the prepro human serum albumin gene.
Figure 5:
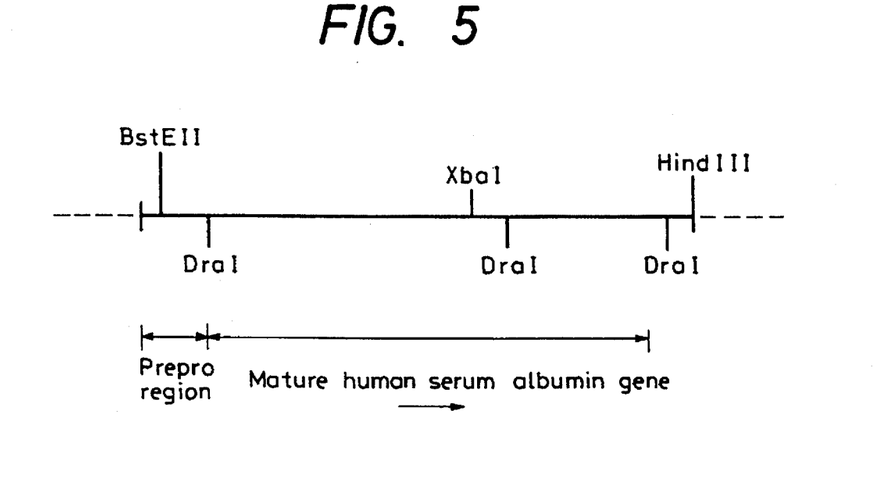
Figure 6:
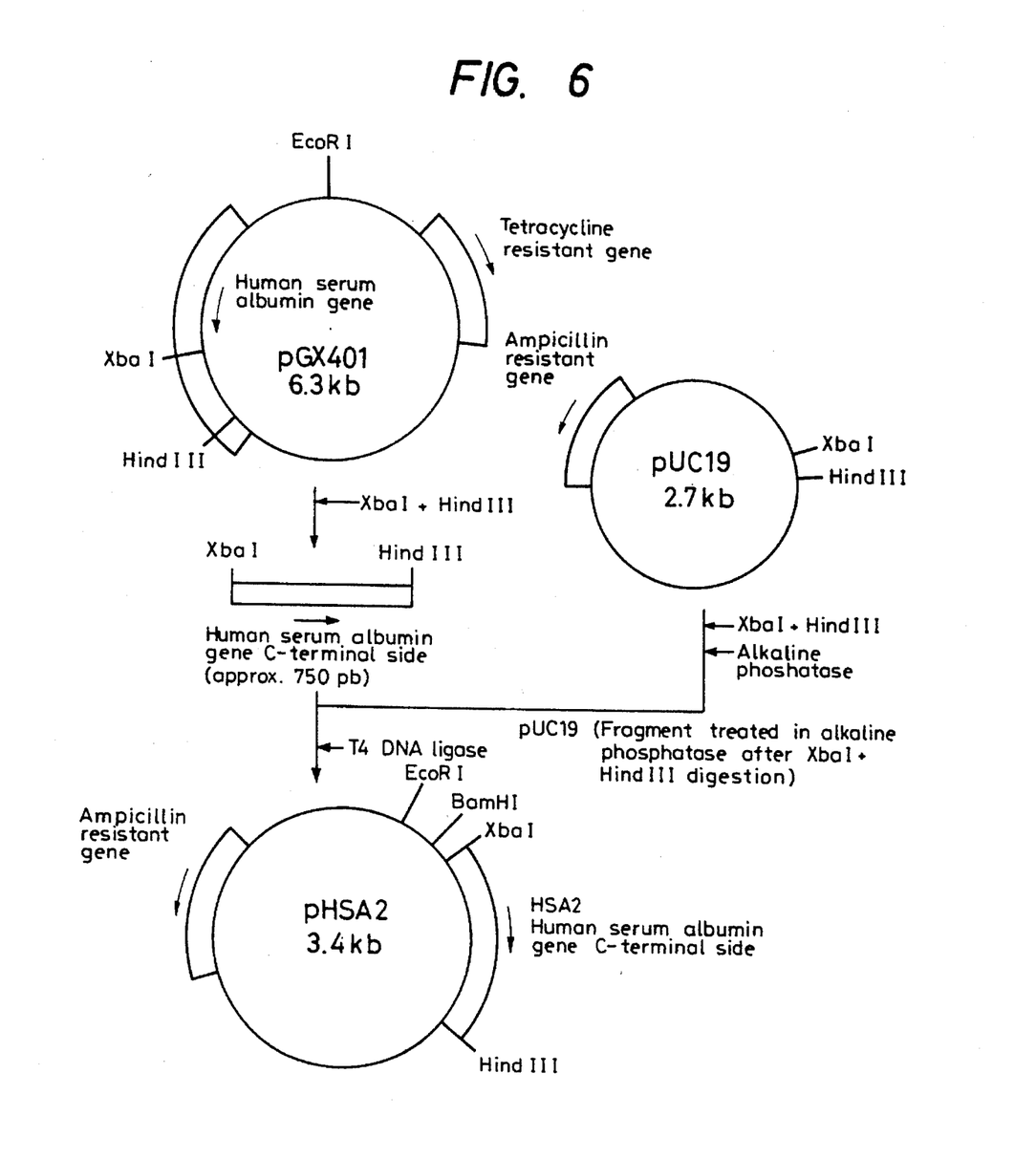
FIG. 6 shows the procedure for making pHSA2, containing the human serum albumin gene C-terminal side from pGX401 and pUC19.

The DNA sequence coding for human serum albumin was derived from the plasmid pGX401 (FIGS. 4 and 5) disclosed in Japanese Patent Application (OPI) No. 29985/87 or EP-A-206733 as follows. pGX401 was digested with the restriction enzymes XbaI and HindIII, and the DNA fragment (HSA2) of about 750 bp coding for the C-terminal side 357Leu to 585Leu of the amino acid sequence of human serum albumin, including the 3' untranslated region, was isolated by electrophoresis. The commercially available plasmid pUC19 was digested with XbaI and HindIII, was treated with alkaline phosphatase to dephosphorylated the 5' terminal and was ligated with HSA2 with T4 DNA ligase. It was introduced into *E. coli* HB101, and from the resulting transformants, a clone having plasmid pHSA2 (as shown in FIG. 6) was obtained.

Upon digesting pGX401 with DraI and XbaI, a DNA fragment of about 1 kb was isolated by electrophoresis. This DNA fragment is the DNA sequence encoding for the N-terminal side $^{12}$Lys to $^{356}$Thr of the amino acid sequence of human serum albumin.

Using the DNA Synthesizer Applied Biosystem model 381A, the following DNA sequence encoding for the N-terminal $^1$Asp to $^{11}$Phe of the amino acid sequence of mature human serum albumin was synthesized by the phosphoramidite method.

amino acid sequence starting from the N-terminal $^1$Asp of mature human serum albumin was obtained.

Figure 7:
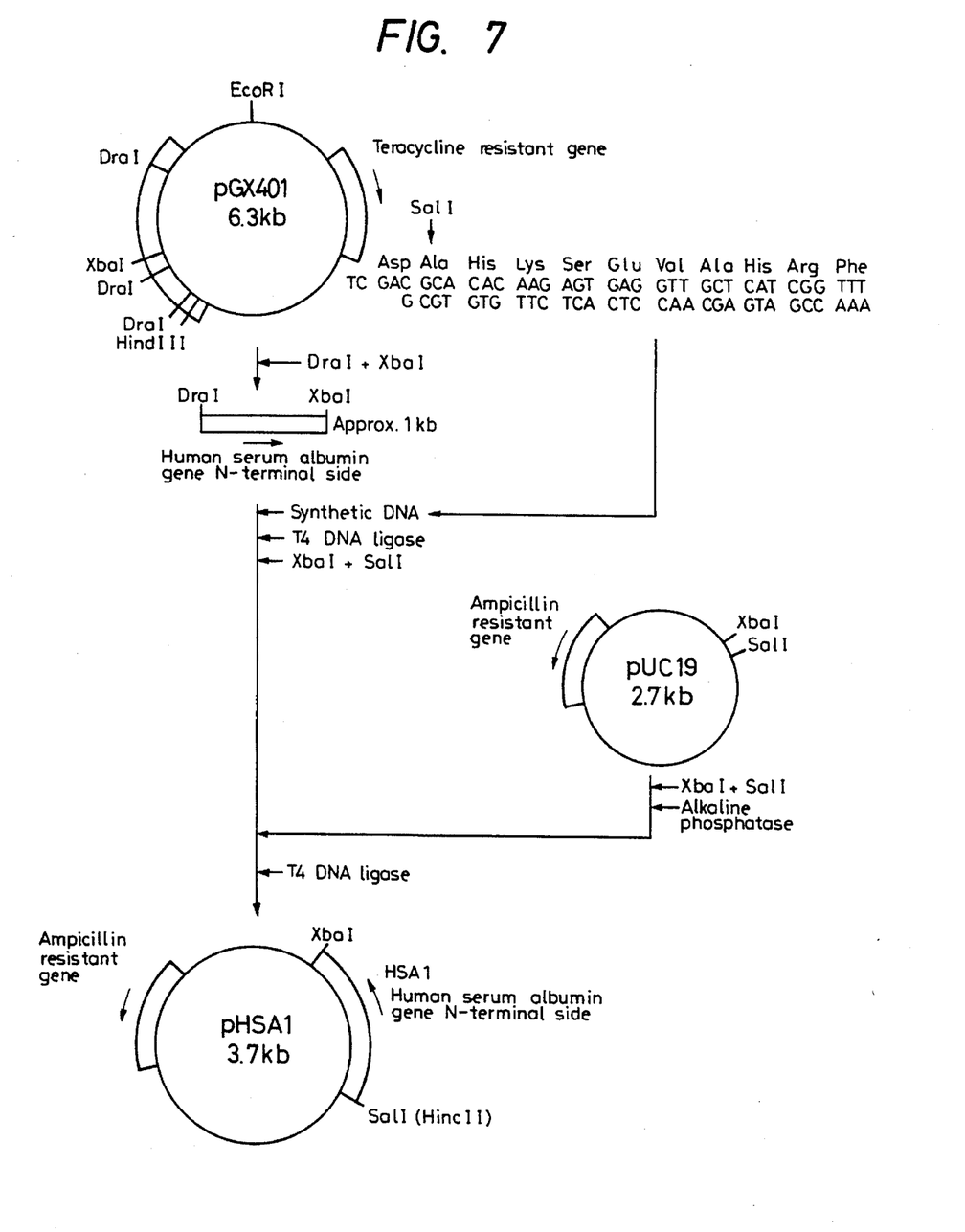
FIG. 7 shows the procedure for making pHSA1, containing the human serum albumin gene N-terminal side, from pGX401 and pUC19.

The 5' terminal of the synthetic DNA was phosphorylated by ATP and T4 polynucleotide kinase. pGX401 was digested with DraI and XbaI and 1 kb DNA fragment was isolated by electrophoresis. This fragment and the phosphorylated synthetic DNA were ligated with T4 ligase, digested with salI and XbaI, and then ligated with pUC19 which was digested with SalI and XbaI and dephosphorylated by CIP. The resulting DNA was introduced into *E. coli* HB101, and from the transformants, a clone having the plasmid pHSA1 (as shown in FIG. 7) was obtained.

(G) Preparation of plasmid DNA for expressing and secreting human serum albumin in yeast The DNA sequence shown in Table 3 below coding for the signal peptide of human serum albumin was synthesized by the phosphoramidite method by the DNA synthesizer Applied Biosystem model 381A.

TABLE 3

| −18 | | −15 | | | | | −10 | | | | | −5 | | | | −1 |
|---|---|---|---|---|---|---|---|---|---|---|---|---|---|---|---|---|
| Met | Lys | Trp | Val | Thr | Phe | Ile | Ser | Leu | Leu | Phe | Leu | Phe | Ser | Ser | Ala | Tyr | Ser |
| GATCCACA ATG AAA TGG GTT ACT TTC ATT TCT TTG TTG TTC TTG TTC TCT TCT GCT TAC TCT |
| GTGT TAC TTT ACC CAA TGA AAG TAA AGA AAC AAC AAG AAC AAG AGA AGA CGA ATG AGA |

Also, the DNA sequence encoding the signal peptide amino acid which was changed to Arg or His, Ala or Pro, Lys or Gly, Val or Cys, Trp or Ser, Ala or Gly in the place of -17, -5, -4, -3, -2 and -1, respectively, was synthesized by the same method (cf. Table 2). The changed DNA sequence lead to produce and secrete the more proper N-terminal side of albumin.

Figure 8:
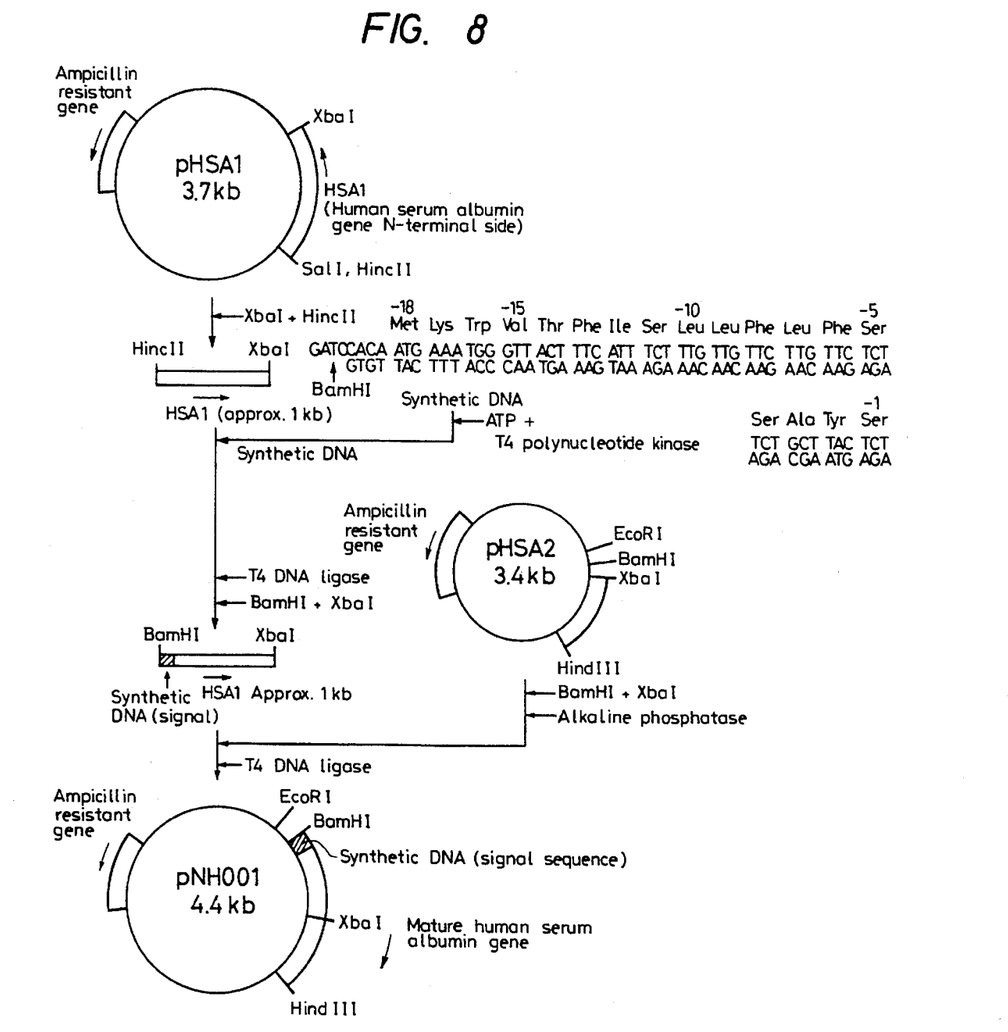
FIG. 8 shows the procedure for making pNH001, containing the signal peptide gene and the mature human serum albumin gene, from pHSA1, pHSA2 and the synthesized signal peptide gene.

The 5' terminal of the synthetic DNA was phosphorylated with ATP and T4 polynucleotide kinase. pHSA1 was digested with XbaI and HincII, and the 1 kb HSA1 DNA fragment encoding for the N-terminal side of human serum albumin was isolated by electrohphoresis. The phosphorylated synthetic DNA and HSA1 were mixed and ligated with T4 DNA ligase, and digested further with XbaI and BamHI. After digesting pHSA2 with XbaI and BamHI, it was treated with alkaline phosphatase. After mixing, these DNAs were ligated with T4 DNA ligase and introduced into *E. coli* HB101 cells. Among the resulting transformants a clone having the plasmid pNH001 (as shown in FIG. 8) was obtained.

Figure 9:
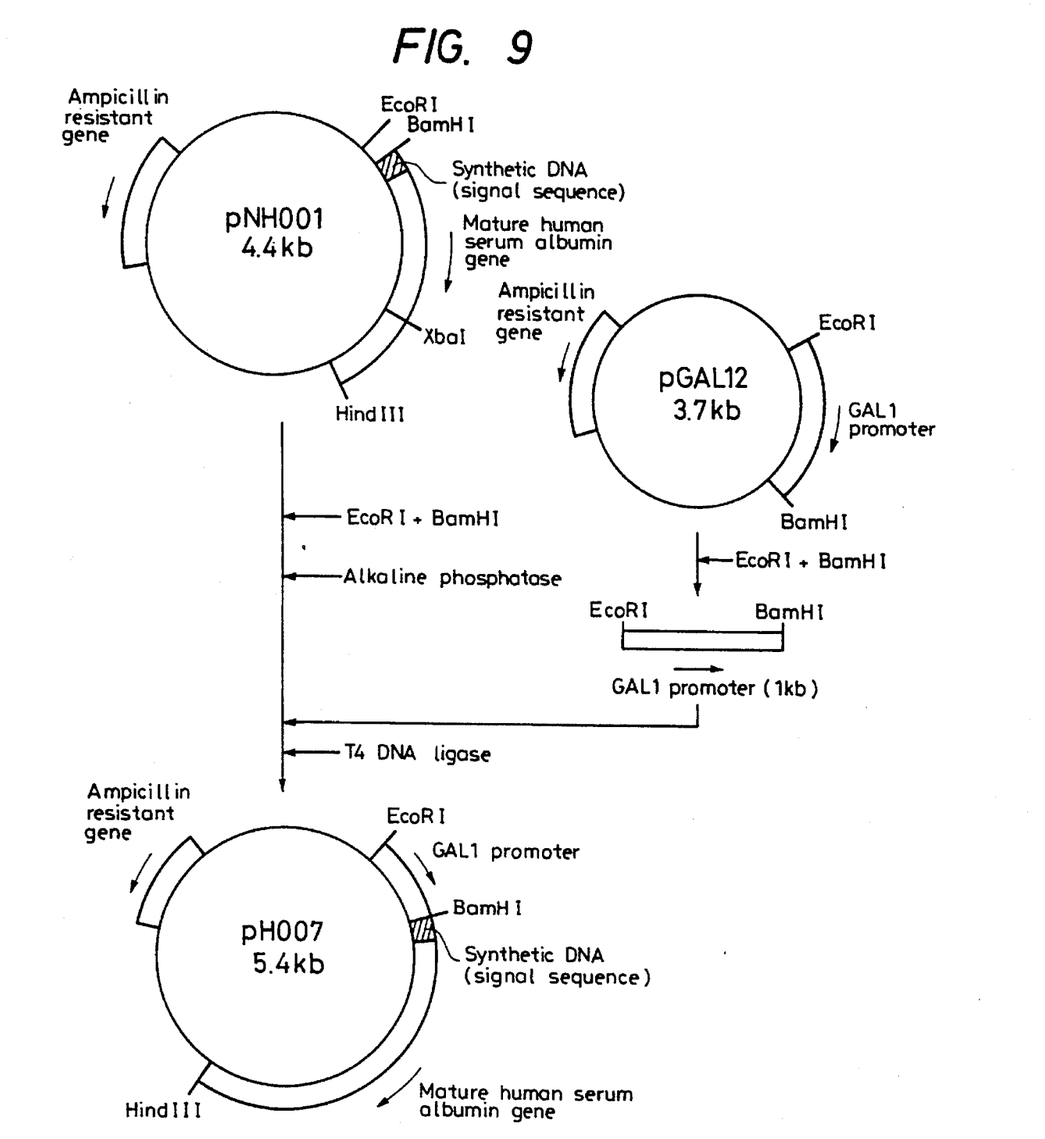
FIG. 9 shows the procedure for making pNH007, containing the GAL1 promoter, signal peptide gene and mature human serum albumin gene, form pNH001 and pGAL12.

After digesting pNH001 with EcoRI and BamHI, it was treated with alkaline phosphatase. Then, pGAL12 was digested with ECgRI and BamHI, a DNA fragment of 1 kb possessing the GAL1 promoter was isolated by electrophoresis, mixed with the treated pNH001 and ligated with T4 DNA ligase. From the resulting transformants, a clone having the plasmid pNH007 (as shown in FIG. 9) was obtained. pNH007 is a plasmid DNA having the DNA

| 1 | 2 | 3 | 4 | 5 | 6 | 7 | 8 | 9 | 10 | 11 |
|---|---|---|---|---|---|---|---|---|---|---|
| Asp | Ala | His | Lys | Ser | Glu | Val | Ala | His | Arg | Phe |
| TC GAC | GCA | CAC | AAG | AGT | GAG | GTT | GCT | CAT | CGG | TTT |
| G | CGT | GTG | TTC | TCA | CTC | CAA | CGA | GTA | GCC | AAA |

The codon for aspartic acid (Asp) in pGX401 was GAT, but GAC was used here. As a result, after ligating the synthetic DNA with the 1 kb DNA fragment derived from pGX401, the SalI site Was regenerated when it was inserted into the SalI-XbaI Site of pUC19. Furthermore, when digested with HincII, the DNA sequence coding for the sequence encoding for the human serum albumin signal peptide located downstream from the GAL1 promoter, the DNA sequence encoding for mature human serum albumin immediately after it, and immediately following that, the 3' untranslated region derived from human serum albumin cDNA inserted in the ECoRI-HindIII site of pUC19.

Figure 10:
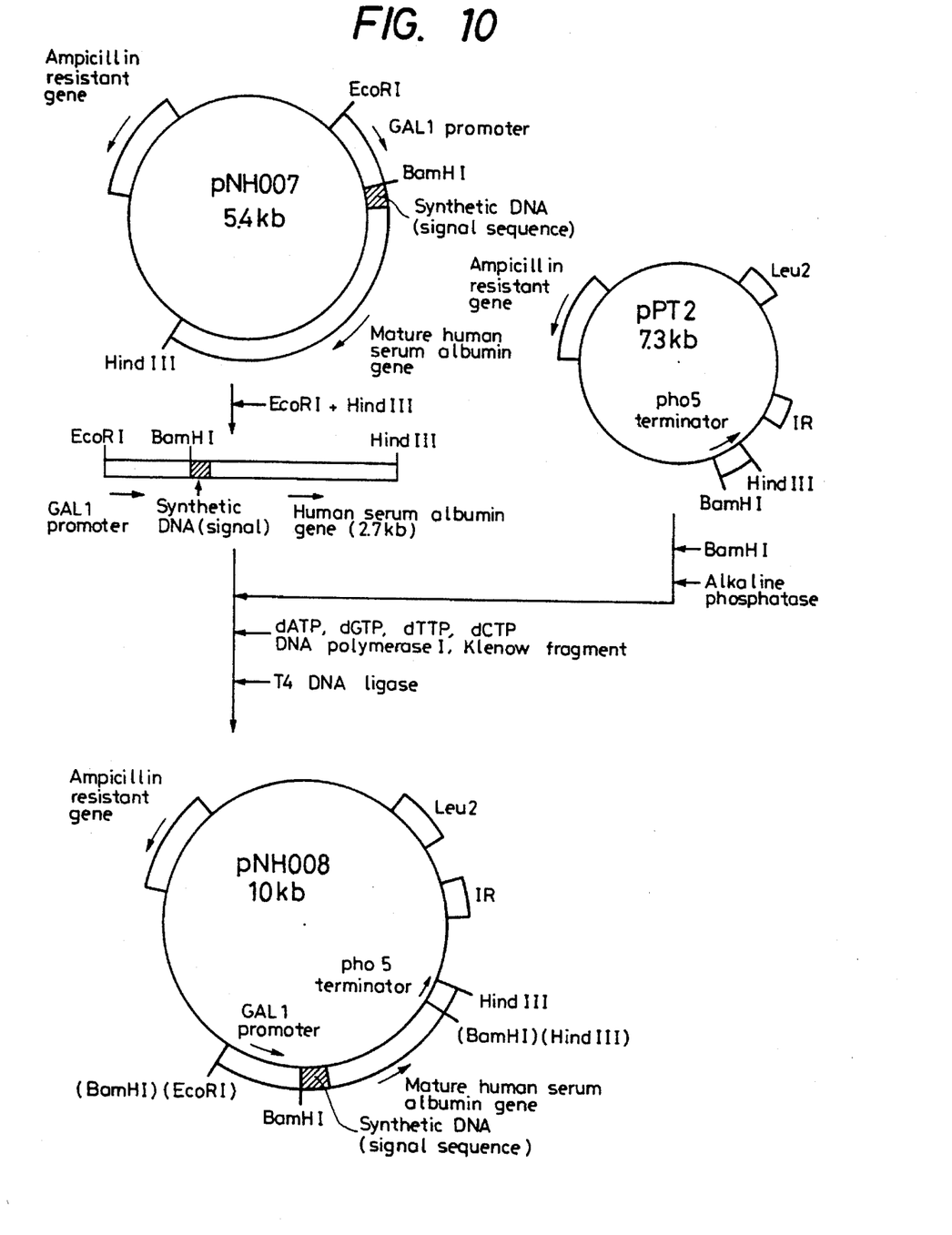
FIG. 10 shows the procedure for making pNH008, containing the GAL1 promoter, signal peptide gene, mature human serum albumin gene and pho5 terminator, from pNH007 and pPT2.

After digesting pNH007 with EcoRI and HindIII, a DNA fragment of 2.7 kb coding for the GAL1 promoter, the signal peptide, mature human serum albumin and the untranslated region was isolated by electrophoresis. Additionally, pPT2 was digested with BamHI and treated with alkaline phosphatase. It was mixed with the 2.7 kb DNA fragment, and the sticky end was repaired by DNA polymerase I, Klenow fragment, in the presence of dATP, dGTP, dTTP, and dCTP. After ligation with T4 DNA ligase, it was introduced into *E. coli* HB101. From the resulting transformants, a clone having the plasmid pNH008 (as shown in FIG. 10) was obtained.

pNH008 is a plasmid capable of self-replication in *E. coli* and yeast and possesses the DNA sequence encoding for the human serum albumin signal peptide and the succeeding mature human serum slbumin protein under the control of the GAL1 promoter functionable in yeast. Furthermore, pNH008 also possesses a gene for ampicillin resistance in *E. coli*, and a gene for fulfilling the nutritional requirement for leucine in yeast, and these genes can be used as selective marker for transformants.

(H) Introduction of plasmid pNH008 into yeast

Plasmid pNH008, for the secretory expression of human serum albumin, was introduced into yeast *Saccharomyces cerevisiae* AH22 (Proc. Natl. Acad. Sci. USA, 75, 1929–1933 (1978)) by the following method.

*S. cerevisiae* AH22 was subjected to shaking culture overnight at 30° C. in 50 ml of YPD medium. (To prepare the medium, 10 g of yeast extract and 20 g of bactopeptone were dissolved in water to make up 900 ml which was sterilized in an autoclave and mixed with 100 ml of 20 w/v % glucose separately sterilized in an autoclave). The cells were precipitated by centrifugation, resuspended in 20 ml of water, and centrifuged again. Next, the cells were suspended in 10 ml of 50 mM dithiothreitol, 1.2M sorbitol, 2 mM EDTA at pH 8.5, and were shaken slowly for 10 minutes at 30° C. The cells were collected by centrifugation, and suspended in 10 ml of 1.2M sorbitol, then centrifuged again for collection. The cells were suspended in 10 ml of 0.2 mg/ml zymolyase 100T, 1.2M sorbitol, 10 mM EDTA, 0.1M sodium citrate at pH 5.8, and were shaken slowly for 1 hour at 30° C. The cells were collected by centrifugation and washed in 10 ml each of 1.2M sorbitol, 10 mM calcium chloride and 1.2M sorbitol, sequentially, and again the cells were collected by centrifugation. The cells were suspended in 1 ml of 10 mM calcium chloride and 1.2M sorbitol. One hundred microliter aliquotes Of suspension were placed in a sterile test tube and mixed with 5 μl (5 μg) of pNH008; the mixture was allowed to stand for 15 minutes at room temperature. After this, it was mixed with 1.2 ml of 20 w/v % polyethylene glycol 4,000, 10 mM calcium chloride, 10 mM tris-hydrochloride at pH 7.5, and after gentle mixing, the mixture was let stand at room temperature for 20 minutes. The cells were collected by centrifugation, suspended in 0.1 ml of YPD medium containing 1.2M sorbitol and 10 mM calcium chloride,-and shaken gently for 30 minutes at 30° C. 1, 5, 10, 20 and 50 μl of suspension were suspended in 45° C.-controlled 10 ml of 1.2M sorbitol, 3 w/v % noble agar, 2 w/v % glucose, and 0.7 w/v % yeast nitrogen base and were spread over plates composed of 1.2M sobitol, 3 w/v % bactoagar, 2 w/v % glucose, and 0.7 w/v % yeast nitrogen base. After the plates solidified, they were subjected to stationary culture for 3 days at 30° C. Formed colonies were collected by a sterile toothpick suspended in 3 ml of 0.7 w/v % yeast nitrogen base and 2 w/v % glucose, and subjected to shaking culture for 2 days at 30° C. One and a half milliliters of suspension was centrifuged, and the cells were collected and suspended in 3 ml of YPG medium. (To prepare the culture, 10 g of yeast extract and 20 g of bactopeptone were dissolved in water to make up 900 ml, sterilized in an autoclave, and mixed with 100 ml of 20 w/v % galactose, sterilized separately in an autoclave.) This was subjected to shaking culture at 30° C. The human serum albumin concentration in the culture supernatant was measured by the RPHA method (as described in European Patent 122,620), and a maximum human serum albumin of 10 μg/ml was detected on the first day.

(I) Cultivation of yeast for the expression and secretion of human serum albumin The yeast *S. cerevisiae* AH22 for the expression and secretion human serum albumin tranformed by pNH008 as mentioned above was cultivated by the following procedure. The recombinant yeast was grown in a plate containing 0.7 w/v % yeast nitrogen base, 2 w/v % glucose and 3 w/v % bactoagar and collected by a platinum loop. It was inoculated into YNB medium 50 ml composed of 0.7 w/v % yeast nitrogen base and 2 w/v % glucose and incubated for 2 days at 30° C. The whole volume was inoculated into 500 ml of YNB medium and incubated for 2 days at 30° C. The cells were collected by centrifugation, and suspended in 500 ml of YPG medium, and subjected to shaking culture at 30° C. A portion of the culture broth was collected after 0, 3, 6, 24 and 48 hours of incubation, and the culture supernatant was obtained by centrifugation. The concentration of human serum albumin secreted into the culture broth was measured by the RPHA method. Secretory expression of human serum albumin was detected beginning the third hour after the start of incubation, and the concentration of human serum albumin in the supernatant was 0.25 mg/l at 6 hours, 20 mg/l at 24 hours, and 160 mg/l at 48 hours.

While the invention has been described in detail and with reference to specific embodiments thereof, it will be apparent to one skilled in the art that various changes and modifications can be made therein without departing from the spirit and scope thereof.

What is claimed is:

1. A method for preparing mature human serum albumin comprising expressing and secreting said mature human serum albumin by yeast transformed by a recombinant DNA comprising a modified human serum albumin signal peptide gene which encodes a modified signal peptide selected from the group consisting of:

MetLysTrpValThrPheIleSerLeuLeuPheLeuPheSerSerValTyrAla,
MetLysTrpValThrPheIleSerLeuLeuPheLeuPheAlaLysValSerAla,
MetLysTrpValThrPheIleSerLeuLeuPheLeuPheProGlyCysTrpAla,
and
MetLysTrpValThrPheIleSerLeuLeuPheLeuPheProGlyValTrpAla, and which does not encode the naturally occurring signal peptide Met-Lys-Trp-Val-Thr-Phe-Ile-Ser-Leu-Leu-Phe-Leu-Phe-Ser-Ser-Ala-Tyr-Ser adjacent to the gene of human serum albumin, a promoter upstream to said modified human serum albumin signal peptide gene and a terminator downstream to said human serum albumin gene, wherein said secreted mature human serum albumin does not contain a signal peptide, and wherein said genes, said promoter and said terminator are linked operably and in proper reading frame.

2. A recombinant DNA encoding a modified human serum albumin signal peptide having the amino sequence selected from the group consisting of:

MetLysTrpValThrPheIleSerLeuLeuPheLeuPheSerSerValTyrAla,
MetLysTrpValThrPheIleSerLeuLeuPheLeuPheAlaLysValSerAla,

-continued

MetLysTrpValThrPheIleSerLeuLeuPheLeuPheProGlyCysTrpAla,
and
MetLysTrpValThrPheIleSerLeuLeuPheLeuPheProGlyValTrpAla, wherein said signal peptide does not have the sequence of the naturally occurring signal peptide, Met-Lys-Trp-Val-Thr-Phe-Ile-Ser-Leu-Leu-Phe-Leu-Phe-Ser-Ser-Ala-Tyr-Ser, adjacent to DNA encoding human serum albumin, a promoter upstream to the modified human serum albumin signal peptide gene and a terminator downstream to the human serum albumin gene, wherein said DNA encoding said peptide, said DNA encoding said human serum albumin, said terminator and said promoter are linked operably and in proper reading frame.

3. A yeast host cell that expresses a mature foreign protein, transformed by a recombinant DNA encoding a modified human serum albumin signal peptide having the amino acid sequence selected from the group consisting of:

MetLysTrpValThrPheIleSerLeuLeuPheLeuPheSerSerValTyrAla,
MetLysTrpValThrPheIleSerLeuLeuPheLeuPheAlaLysValSerAla,
MetLysTrpValThrPheIleSerLeuLeuPheLeuPheProGlyCysTrpAla,
and
MetLysTrpValThrPheIleSerLeuLeuPheLeuPheProGlyValTrpAla, wherein said signal peptide does not have the sequence of the naturally occurring signal peptide, Met-Lys-Trp-Val-Thr-Phe-Ile-Ser-Leu-Leu-Phe-Leu-Phe-Ser-Ser-Ala-Tyr-Ser, adjacent to DNA encoding human serum albumin, a promoter upstream to the modified human serum albumin signal peptide gene, a terminator downstream to the human serum albumin gene, wherein said DNA encoding said peptide, said DNA encoding said human serum albumin, said terminator and said promoter are linked operably and in proper reading frame.

4. A modified human serum albumin signal peptide sequence having an amine acid sequence selected from the group consisting of:

MetLysTrpValThrPheIleSerLeuLeuPheLeuPheSerSerValTyrAla,
MetLysTrpValThrPheIleSerLeuLeuPheLeuPheAlaLysValSerAla,
MetLysTrpValThrPheIleSerLeuLeuPheLeuPheProGlyCysTrpAla,
and
MetLysTrpValThrPheIleSerLeuLeuPheLeuPheProGlyValTrpAla, wherein said signal peptide does not have the sequence of the naturally occurring signal peptide, Met-Lys-Trp-Val-Thr-Phe-Ile-Ser-Leu-Leu-Phe-Leu-Phe-Ser-Ser-Ala-Tyr-Ser.

* * * * *